United States Patent

Semm

Patent Number: 5,201,739
Date of Patent: Apr. 13, 1993

[54] MEDICAL INSTRUMENT

[75] Inventor: Kurt Semm, Kiel, Fed. Rep. of Germany

[73] Assignee: WISAP Gesellschaft fur Wissenschaftlichen Apparatebau mbH, Sauerlach, Fed. Rep. of Germany

[21] Appl. No.: 685,051

[22] Filed: Apr. 15, 1991

Related U.S. Application Data

[63] Continuation-in-part of Ser. No. 352,471, May 16, 1989, abandoned.

[30] Foreign Application Priority Data

May 17, 1988 [DE] Fed. Rep. of Germany ....... 3816798

[51] Int. Cl.⁵ .............................................. A61B 17/28
[52] U.S. Cl. ...................................... 606/106; 606/110; 606/174; 606/206
[58] Field of Search ................ 606/45, 174, 305, 205, 606/206, 207, 106, 110, 175, 52; 294/19.1, 104

[56] References Cited

U.S. PATENT DOCUMENTS

| | | |
|---|---|---|
| 86,016 | 1/1869 | Howell . |
| 3,834,021 | 9/1974 | White et al. . |
| 4,122,856 | 10/1978 | Mosior et al. . |
| 4,258,716 | 3/1981 | Sutherland . |
| 4,433,687 | 2/1984 | Burke et al. . |
| 4,449,518 | 5/1984 | Konomura et al. . |
| 4,499,899 | 2/1985 | Lyons, III . |
| 4,590,936 | 5/1986 | Straub et al. . |
| 4,644,651 | 2/1987 | Jacobsen . |
| 4,646,751 | 3/1987 | Maslanka ............................ 128/751 |
| 4,655,219 | 4/1987 | Petruzzi .............................. 606/206 |
| 4,662,371 | 5/1987 | Whipple et al. . |
| 4,674,501 | 6/1987 | Greenberg . |
| 4,760,848 | 8/1988 | Hasson . |
| 4,830,002 | 5/1989 | Semm . |

FOREIGN PATENT DOCUMENTS

| | | |
|---|---|---|
| 170360 | 8/1905 | Fed. Rep. of Germany . |
| 8319104.6 | 12/1983 | Fed. Rep. of Germany . |
| 31672 | 9/1904 | Switzerland . |
| 736949 | 5/1980 | U.S.S.R. . |

*Primary Examiner*—Robert A. Hafer
*Assistant Examiner*—Brian E. Hanlon
*Attorney, Agent, or Firm*—Keck, Mahin & Cate

[57] ABSTRACT

The present invention relates to a medical instrument. Since, in the case of instruments operated by gripping disks, a conventional spring preloading has not been adequate for an effective closing movement, an improvement is proposed here. This consists of so articulating a front gripping disk to an instrument member that, through a manually applied axially rearward movement of the gripping disk, the instrument members are closed.

10 Claims, 3 Drawing Sheets

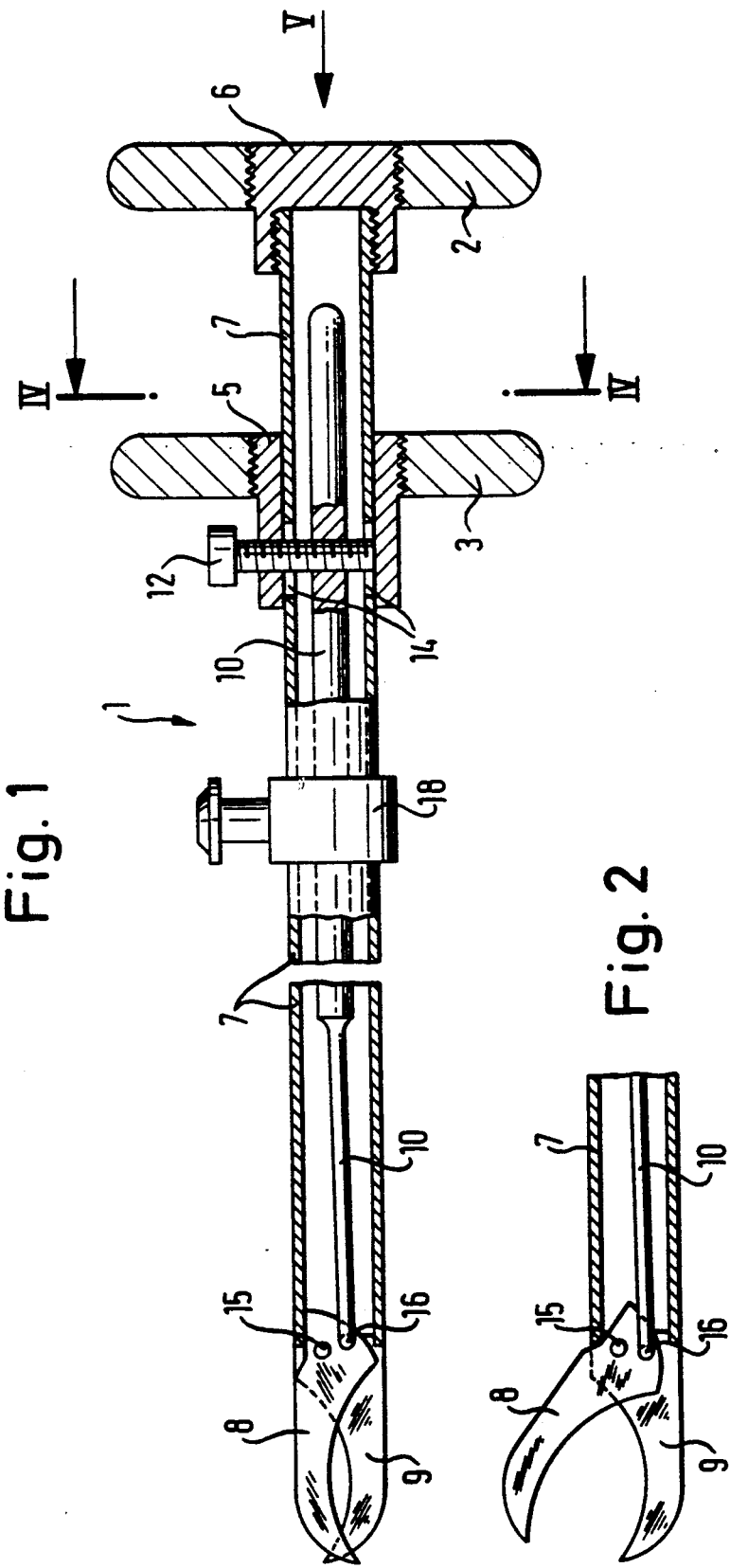

MEDICAL INSTRUMENT

This application is a Continuation-in-part of U.S. patent application Ser. No. 07/352,471, filed May 16, 1989, abandoned on Apr. 16, 1991.

BACKGROUND OF THE INVENTION

A medical instrument generally relating to the subject matter of this invention is known from U.S. Pat. No. 4,830,002, issued May 16, 1989. The known instrument is specially constructed with respect to rotatability of the proximal gripping members or disks, so that, if necessary, the distal members, which may be constructed as forceps members, can be rotated into a more suitable working position, due to the rotatability.

In the known instrument, the axial displaceability of the forceps members, in the case of a stationarily held instrument sleeve and front gripping member, is brought about by the rear gripping member. As the rear gripping member, constructed as a disk, is spring preloaded so that in the inoperative position, the distal forceps members are drawn into the instrument sleeve. The spring tension conventionally determines the forceps force which can be applied on the distal side. As a result of a minimum spacing present between the proximal gripping members, it is still possible, in the case of the known instrument, to increase the spring tension, on gripping or cutting off a piece of tissue with the forceps members, by manually moving the distal gripping member rearwards by inserting the fingers between the proximal gripping members.

However, the latter procedure is not optimum from an ergonomic standpoint, because the front gripping member must be grasped by the fingers on its distal side, whilst the surface of the hand rests against the rear part of the rear gripping disk. The insertion of fingers into the gap between the two gripping members is, consequently, relatively unergonomic.

Other medical instruments, similar to that already mentioned are known from German application 83 19 104.6 Ul, German Patent 170,360, U.S. Pat. No. 86,016 and Swiss Patent 31,672. It is a common feature of these other medical instruments that an operating rod, axially displaceable in the instrument sleeve, is under spring preloading. The operating rod is, in these instruments, rigidly connected to the proximal, rear gripping member. Thus, in order to open the forceps members, it is always necessary to move the rear gripping member axially in the distal direction towards the front gripping member connected to the instrument sleeve. The corresponding spring tension causes the grasping or closing movement of the forceps members to be carried out.

SUMMARY OF THE INVENTION

Considering these disadvantages of the prior art, the object of the present invention is to construct a medical instrument of the aforementioned type which can be a gripping, clamping or cutting instrument so that, if necessary, it is ergonomically possible to significantly increase the force acting on the distal instrument members, optionally in addition to a spring tension. The medical instrument, moreover, has a simple construction.

An essential basic principle of the invention is to depart from the hitherto conventional displaceability of the rear, proximal gripping member and, instead, keep the same stationary, whilst applying a higher force to the distal instrument members via the front gripping member as a result of an axial closing movement between the two gripping members. The distal instrument members can be of a random nature, e.g., gripping, clamping, cutting or forceps members, so that the gripping members are virtually universally usable in medical instruments of this type.

In order to be able to carry out the aforementioned movement of the gripping members, the rear gripping member is rigidly connected to an instrument sleeve. The front gripping member is connected to an operating rod, which is at least slightly axially displaceable in the instrument sleeve and which has an articulation for the distal instrument member or members, so that through a forward axial displacement of the operating rod an opening movement of the instrument is performed, whilst an axial rearward displacement brings about the closing movement. This means that the distal area of the front gripping member can be grasped by the fingers of the operating surgeon and by drawing backwards, i.e., compressing the two gripping members, it is possible to increase the closing force on the distal instrument members, e.g., the forceps members or shear blades The rear side of the rear gripping member engages against the inner hand surface.

In the case of the inventive medical instrument, having a constructional principle which is usable in a multifunctional manner and which is, e g., suitable for gripping, clamping or cutting, there is no longer any need to maintain the conventional orientation of the fingers or human hand typically used when shearing or cutting. In fact, the medical instrument can function correspondingly by pressure or pulling action of the fingers when the instrument is in any "rotation position," i.e., it can function correctly over 360°. Therefore, without changing the finger orientation, which would normally lead to a corresponding change in hand or forearm orientation, the ergonomic operation enables the surgeon to effortlessly operate the medical instrument by 360° without any functional restriction. Thus, for the medical instrument, which can, e.g., be a gripping, clamping or cutting instrument, an operating possibility of the corresponding distal instrument members is provided, independently of whether its movement requires a pressing or a pulling movement and without any changed hand or forearm orientation being necessary Therefore the surgeon can assume the position which is ergonomically optimum for the hand, so that a virtually fatigue-free, uncramped handling of the medical instrument is possible.

For simplification, the multifunctional instrument will be referred to hereinafter as a medical instrument, whilst in exemplified manner the distally operable instrument members are referred to as forceps members.

In order to ensure that the surgical instrument is always closed on introduction into the operating region, a spring can be provided, which rearwardly biases the front gripping member into the closed or inoperative position of the forceps members. On opening the forceps members, it is, therefore, necessary to forwardly axially displace the front gripping member. If the spring tension is not sufficient on grasping or cutting off a tissue region, the gripping, clamping, cutting or forceps force can be increased in the manner previously described.

In a simple embodiment of the invention, one forceps member is rigidly connected to the instrument sleeve, whilst only the second forceps member is directly or indirectly operable by means of a lever articulation. If, as an alternative, both forceps members are to be moved, it is obviously possible to carry out the articulation by means of a corresponding central member. The scissor-like operation of both forceps members, which can e.g. take place by means of a parallelogram mechanism, permits a better force application, because the lever arm is improved.

The movable forceps member is appropriately mounted on a pivot bearing formed by a pivot pin fixed to the sleeve. The articulation of the operating rod in the movable gripping member appropriately takes place on the opposite side of the pivot bearing from the opening movement.

Other control elements, such as, e.g., an instrument shank or the like, can be used in place of the operating rod.

The non-positive coupling between the front gripping member, which is appropriately constructed as a gripping disk, and the operating rod takes place by a substantially radial driving engagement means movable in an axial recess of the instrument sleeve. The driving engagement can be obtained directly by a pin located radially in the inner bore of the gripping disk. In the case of improving the sliding movement on the instrument sleeve, for which purpose the gripping member is fixed to a bush, the driver can, e.g , be realized by a screw, particularly a countersunk or grub screw, passed radially through the bush and the operating rod.

The design of the gripping members as gripping disks permits gripping over 360° and, therefore, ergonomic positioning of the gripping members in the hand. It is advantageous, for adjusting the spring tension, to be able to displaceably fix the abutment for supporting the spring in an axial manner to the instrument sleeve.

With a view to the forced transmission and a short axial displacement path, the movable forceps member is connected, in a lever arm-like manner, with a second lever arm for the articulation of the operating rod engaging thereon under an obtuse or right angle. A one-piece forceps member is appropriately provided for this On only operating one forceps member, the spacing between the rotation axis thereof and the articulation point of the forceps member is kept at a maximum. Thus, the articulation and pivot or rotation point are appropriately located in the vicinity of the maximum instrument sleeve diameter. This leads to a favorable lever arm action for transmitting the force to one operable forceps member.

The invention is described in greater detail hereinafter with respect to two diagrammatic embodiments. The inventive medical instrument, which can be used as a gripping, clamping, cutting or forceps instrument, is referred to as a forceps instrument hereinafter for simplification purposes This is considered to cover the most varied constructional embodiments thereof.

BRIEF DESCRIPTION OF THE DRAWING

FIG. 1 is an axial section through a first embodiment of the inventive medical instrument, e.g., a forceps instrument, in which the forceps members are closed.

FIG. 2 shows partially the distal area of the instrument shown in FIG. 1, with the forceps members open.

DESCRIPTION OF THE PREFERRED EMBODIMENTS

Figure 3:
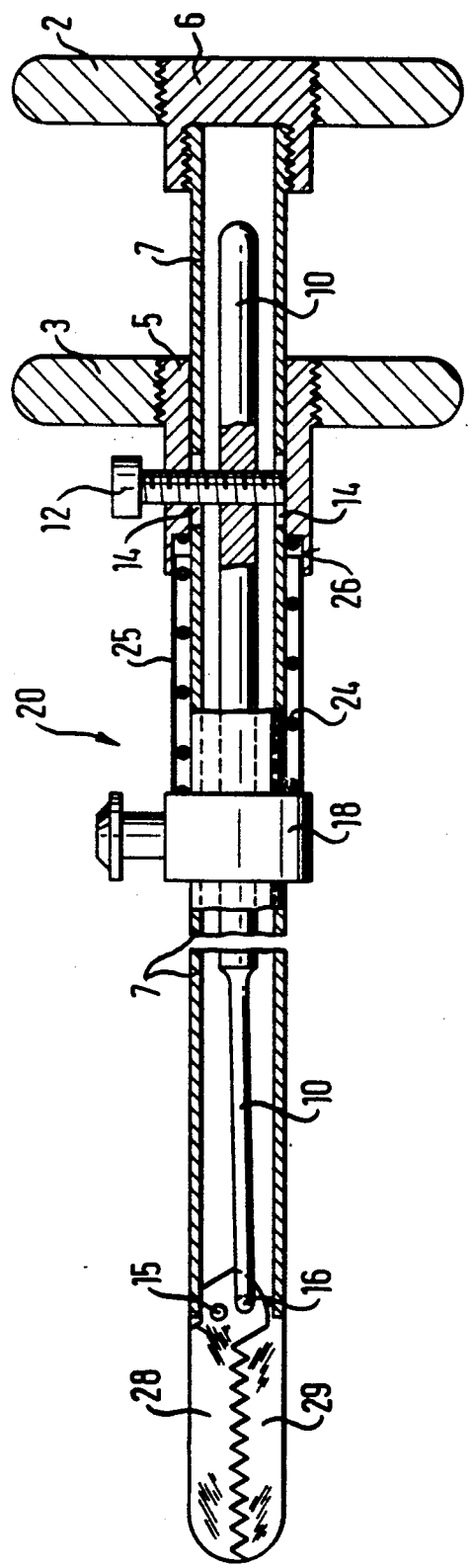
FIG. 3 is a comparable axial section through a second embodiment of the inventive instrument, having spring preloading, in which the forceps members are closed in the inoperative position.

The forceps instrument 1, shown in axial section in FIG. 1, essentially has a tubular instrument sleeve 7, in which an operating rod 10 is displaceable over at least a small axial distance. To the rear end of the instrument sleeve 7 is fitted, e.g., by screwing, a blind bush 6. To the latter is rigidly fixed the rear gripping disk 2, and it is also possible to provide a screw connection for this.

At the distal end of the forceps instrument, a forceps member is rigidly fixed to the instrument sleeve, e.g., by welding. The second and, in the present embodiment, upper forceps member 8 is pivotable about a pivot pin 15, which can be riveted to the instrument sleeve 7.

Since, in the embodiment illustrated in FIG. 1, the swivel bearing 15 is located slightly above the median longitudinal axis, the operating rod 10 engages, via an articulation 16, with forceps member 8 below the bearing. Articulation 16 conventionally also has a pin about which the rear part of the forceps member 8 can move slightly. With the forceps members 8 and 9 in the closed state, as shown in FIG. 1, they are aligned in the axial direction with the outer face of the instrument sleeve 7. The rear part, i.e., the pivoting part, of the movable forceps member 8 roughly corresponds to the internal diameter of the instrument sleeve 7. The proximal edge is rounded, so that also in the case of an opening movement, there is no projection over the external diameter of the instrument sleeve 7.

The slightly crescent-shaped forceps members 8 and 9, according to FIGS. 1 and 2 can, e.g., be parts of surgical hook shears.

A front gripping member 3, fixed to a bush 5, e.g., via a thread, is positioned at a distance from the rear gripping member for the axial displacement of operating rod 10. The force transmission or rigid coupling between the front gripping member 3 and the operating rod 10 takes place by means of a screw 12, guided radially through the bush and the rear part of operating rod 10. Appropriately, screw 12 engages with the facing inner face of bush 5. The axial displaceability with respect to the stationary instrument sleeve 7 is made possible since, on each side of the sleeve, an axial recess 14 or a corresponding slot having the approximate size of the screw diameter is provided.

The forceps members 8 and 9 of the forceps instrument according to FIG. 1 are opened by increasing the axial spacing between the front and rear gripping members. By moving the gripping member 3 towards the distal end on instrument sleeve 7, the operating rod 10 is moved forwards by the rigid coupling. Thus, via articulation 16, a lever movement is exerted on the movable forceps member 8, so that the latter can be opened into the position shown in FIG. 2. The operating rod 10, which is provided with a larger diameter in the rear area, particularly in the vicinity of the driving pin, undergoes a material weakening in the front area with a slight deflection out of the median longitudinal plane, so that it can act on articulation point 16 in a spaced manner with respect to the median axis and pivot pin 15. FIG. 2 shows that the rear part of the movable forceps member 8 is designed in such a way that the opening and closing movement can take place in the diameter region of instrument sleeve 7.

In the second embodiment of the forceps instrument 20 according to FIG. 3, the same references as in FIG. 1 are used for the same components and units. The essential difference between this second embodiment and the first embodiment of the forceps instrument is that when the forceps members 28 and 29 are in the closed position, the front gripping member 3 is spring biased rearwards. The corresponding spring 24 is supported against an abutment 18, which is axially adjustable, but arrestable, on the instrument sleeve 7. Abutment 18 can be constructed as a displaceable ring. In the embodiment of FIG. 3, spring 24 is arranged around the instrument sleeve 7, being surrounded by an outer sleeve 25. Outer sleeve 25 engages in a fixed or movable manner with respect to the abutment 18 and extends rearwards into a circular groove 26 of bush 5.

The forceps members 28 and 29 shown in FIG. 3 have a sawtooth-like contour, as is, e.g., required for peritoneal shears.

Otherwise, the construction according to FIG. 3 corresponds to that of FIG. 1. In the closed position according to FIG. 3 the front gripping member is consequently rearwardly biased by spring 24. Thus, for opening the forceps members 28, 29, it is necessary to axially displace the gripping member 3 towards the distal end of instrument sleeve 7. However, it is important to note here that when the spring tension acting on the forceps members 28 and 29 is not adequate, the front gripping member 3 can be moved manually rearwards, which corresponds to a closing movement of the hand, so that increased forceps force is sufficient for separating or cutting, e.g., tissue.

The medical forceps instrument is essentially made from V2A-steel or a similar material for sterilization purposes. The gripping members 2 and 3, which are appropriately constructed as gripping disks, can be ergonomically designed, so that the rear gripping member roughly conforms to the inner hand surface, whilst the distal surface and marginal region of the front gripping member can have gripping zones or depressions for gripping and operating by means of the fingers. Such will be explained further in connection with FIGS. 4 and 5. The design scope with respect to this instrument is not limited to purely forceps instruments, such as hook shears, peritoneal shears, biopsy and similar forceps, atraumatic grippers, claw grippers, etc., and instead, in general terms, relates to the design of one or two-member spreading instruments used in the medical field.

Figure 4:
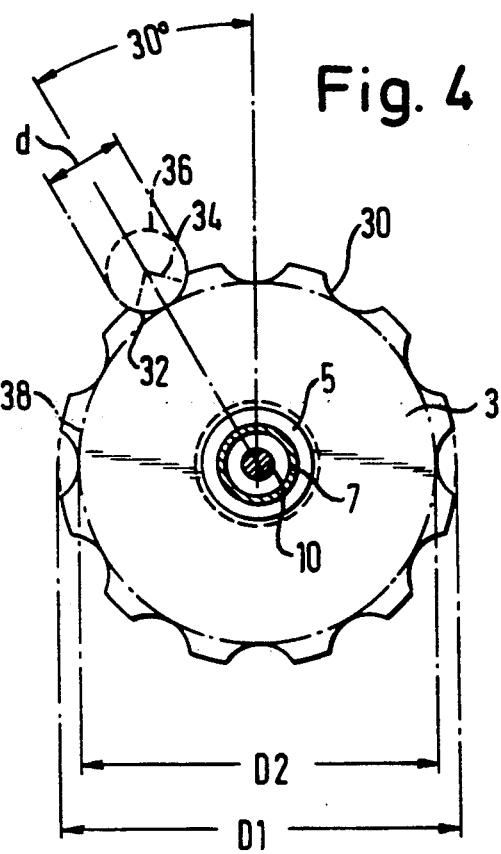
FIG. 4 is a cross-sectional view of the instrument shown in FIG. 1 as seen along section line IV—IV.
Figure 5:
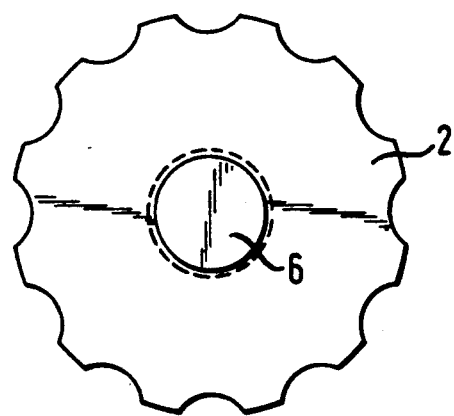
FIG. 5 is an end view of the instrument shown in FIG. 1 as seen in the direction of arrow A.

The equipping of the forceps instrument with such circular gripping disks as gripping members 2, 3 has the major advantage that, in the case of a necessary rotation of the distal forceps members 28 and 29 as a result of medical circumstances in the operating area, the complete forceps instrument can be turned, e.g., in the trocar. Even following such an operatively necessary rotation of the instrument, the surgeon still has the same ergonomic conditions, due to the disk-like and, in particular, circular, gripping members. This is an important advantage compared with known forceps instruments with respect to shear-like gripping members at the proximal end of forceps instruments and the manual increase of the forceps forces by drawing the front gripping member rearwards. Referring now to FIGS. 4 and 5, the specific contour of the circumferential edges of each of the circular gripping disks 2 and 3 of FIG. 1 is illustrated. Each of the disks 2 and 3 has an outermost diameter of approximately 50 mm. As is clear from a comparison of FIGS. 4 and 5, the disks 2 and 3 have substantially identical contours. Referring to FIG. 4, the disk 3 is shown as including a plurality, and, as illustrated, twelve, arc-like indentations or part-circular recesses 30 evenly distributed about its circumference at evenly spaced locations. Since, in the illustrated embodiment, twelve recesses 30 are provided, each recess is spaced from adjacent recesses by 30°.

As noted above, each recess 30 is part-circular. Each recess 30 has an edge which coincides with the included arc 32 of a sector 34 of an imaginary circle 36, which has a diameter d of approximately 10 mm. Each recess 30 extends, at most, about 2 mm radially inwardly from the outermost circumferential edge of disk 3. Thus, the innermost points of recesses 30 collectively lie on an imaginary circle 38, which has a diameter D2 of approximately 46 mm. As mentioned above, disk 2 has a contour substantially identical to that of disk 3. The disks 2 and 3 of the embodiment shown in FIG. 3 may be formed similarly. By providing circular gripping disks 2 and 3 with the particular circumferential edge contours described above, handling of the instrument 1 or 20 is improved, since the user can securely grip either disk 2 or disk 3 with two, three or more fingers of one hand at any location over its 360° outer circumference with a decreased likelihood that the disk will slip relative to the user's fingers.

I claim:

1. A medical instrument comprising:
   an outer instrument sleeve having a longitudinal axis,
   an inner operating rod axially movable within said outer instrument sleeve,
   forcep instrument members located at a distal end of said outer instrument sleeve,
   two gripping members, both of said gripping members being operable by one hand and arranged at a proximal end of said outer instrument sleeve,
   said two gripping members being constructed as a substantially circular rear gripping disk and a substantially circular front gripping disk, the disks being disposed in parallel planes substantially perpendicular to said axis,
   said rear gripping disk, in operation, being disposed in a palm of a hand of a user while said front gripping disk is gripped by fingers of the hand of the user at any location over its 360 degree outer circumference,
   said rear gripping disk being rigidly connected to said outer instrument sleeve,
   said front gripping disk being rigidly connected to said inner operating rod for operating said forcep instrument members,
   said front gripping disk being moved rearwardly by the fingers of the user towards said rear gripping disk when closing the hand of the user for applying a force to said forcep instrument members.

2. An instrument according to claim 1, and further comprising a spring for biasing said front gripping disk toward said rear gripping disk, wherein the spring is supported on an abutment of the outer instrument sleeve.

3. An instrument according to claim 1, wherein one of said forcep instrument members is rigidly mounted on the distal end of the outer instrument sleeve and the other of said forcep instrument members has an articulation point located on the operating rod.

4. An instrument according to claim 3, wherein said other of said forcep instrument members has a pivot bearing fixed to the outer instrument sleeve and the articulation point of the operating rod is on a lever arm of said other of said forcep instrument members.

5. An instrument according to claim 1, wherein the front gripping disk is rearwardly biased by means of a spring.

6. An instrument according to claim 2, wherein the abutment is arranged in an axially adjustable manner on the outer instrument sleeve for adjusting the spring tension.

7. An instrument according to claim 4, wherein the pivot bearing and the articulation point of the operating rod on the lever arm of said other of said forcep instrument members have a maximum spacing less than the instrument sleeve diameter.

8. An instrument according to claim 1, wherein at least one of said rear gripping disk and said front gripping disk has a plurality of part-circular recesses distributed about its outer circumference for receiving fingers of a user.

9. A medical instrument comprising:
an outer instrument sleeve having a longitudinal axis,
an inner operating rod axially movable within said outer instrument sleeve,
forcep instrument members located at a distal end of said outer instrument sleeve,
two gripping members, both of said gripping members being operable by one hand and arranged at a proximal end of said outer instrument sleeve,
said two gripping members being constructed as a substantially circular rear gripping disk and a substantially circular front gripping disk, said disks being disposed in parallel planes perpendicular to said axis,
said rear gripping disk, in operation, being disposed in a palm of a hand of a user while said front gripping disk is gripped by fingers of the hand of the user at any location over its 360 degree outer circumference,
said rear gripping disk being rigidly connected to said outer instrument sleeve,
said front gripping disk being rigidly connected to said inner operating rod for operating said forcep instrument members,
said front gripping disk being moved rearwardly by the fingers of the user towards said rear gripping disk when closing the hand of the user for applying a force to said forcep instrument members,
said operating rod being connected by means of a radial driving member to the front gripping disk,
said radial driving member being axially displaceably guided in a slot formed in the outer instrument sleeve.

10. An instrument according to claim 9, wherein at least one of said rear gripping disk and said front gripping disk has a plurality of part-circular recesses distributed about its outer circumference for receiving fingers of a user.

* * * * *